United States Patent [19]

Schubert

[11] Patent Number: 5,530,153
[45] Date of Patent: Jun. 25, 1996

[54] PROCESS FOR PREPARATION OF ARYLDIMETHYL (3-ARYL-PROPYL)SILANES

[75] Inventor: Hans H. Schubert, Frankfurt am Main, Germany

[73] Assignee: Hoechst Aktiengesellschaft, Germany

[21] Appl. No.: 379,037

[22] Filed: Jan. 27, 1995

Related U.S. Application Data

[60] Continuation of Ser. No. 145,247, Oct. 29, 1993, abandoned, which is a division of Ser. No. 398,058, Aug. 24, 1989, Pat. No. 5,286,862.

[30] Foreign Application Priority Data

Aug. 26, 1988 [DE] Germany ............... 38 28 926.1

[51] Int. Cl.$^6$ ........................................... C07F 7/08
[52] U.S. Cl. ................. 556/489; 556/440; 556/445; 546/14; 549/214
[58] Field of Search .................... 556/489, 440, 556/445; 549/214; 546/14

[56] References Cited

U.S. PATENT DOCUMENTS

| | | | |
|---|---|---|---|
| 4,053,497 | 10/1977 | Fory et al. | 556/489 |
| 4,242,272 | 12/1980 | Koga et al. | 556/489 |
| 4,269,993 | 5/1981 | Ohtake et al. | 556/489 X |
| 4,469,881 | 9/1984 | Arkles | 556/489 X |
| 4,695,643 | 9/1987 | Oertle et al. | 556/489 X |
| 4,709,068 | 11/1987 | Sieburth . | |
| 4,864,027 | 9/1989 | Shubert et al. | 546/14 |

FOREIGN PATENT DOCUMENTS

| | | |
|---|---|---|
| 0224024 | 10/1986 | European Pat. Off. . |
| 0249015 | 12/1987 | European Pat. Off. . |
| 3604781 | 8/1987 | Germany . |
| 86/8101 | 10/1986 | South Africa . |
| 87/2878 | 4/1987 | South Africa . |
| 88/6875 | 9/1988 | South Africa . |
| 1170888 | 11/1969 | United Kingdom . |

OTHER PUBLICATIONS

Chemical Abstracts 97:7137q (1982).
Journal of Organic Chemistry, Musolf et al., Sep. 1964, pp. 2519–2524.
Houben–Weyl, Methoden der Organischen Chemie, vol. 13/5, 1980, p. 45.
Wuhan daxne xuebao. Ziran kexue ban 1981 (4), pp. 61–67.
Chemical Abstracts 101:23576K (1984).

*Primary Examiner*—Paul F. Shaver
*Attorney, Agent, or Firm*—Curtis, Morris & Safford

[57] ABSTRACT

Process for the preparation of aryldimethyl(3-arylpropyl)silanes by a route comprising hydrosilylation followed by a modified Grignard reaction.

1 Claim, No Drawings

PROCESS FOR PREPARATION OF ARYLDIMETHYL (3-ARYL-PROPYL)SILANES

This application is a continuation of application Ser. No. 08/145,247, filed Oct. 29 1993, now abandoned which is a divisional of application Ser. No. 07/398,058, filed Aug. 24, 1989 now U.S. Pat. No. 5,286,862.

The present invention relates to a process for the preparation of compounds of the formula I

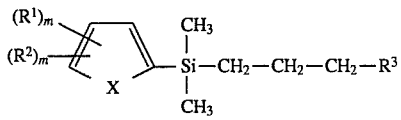

where X is CH=CH, N=CH, CH=N or S, $R^1$ and $R^2$ independently of one another are H, halogen, ($C_1$–$C_4$) alkyl, ($C_1$–$C_4$) alkoxy, ($C_1$–$C_4$) alkylthio, ($C_1$–$C_4$) haloalkyl, ($C_1$–$C_4$) haloalkoxy, ($C_1$–$C_4$) haloalkylthio or the bivalent methylenedioxy group, $R^3$ is a radical of the formulae (A), (B) or (C)

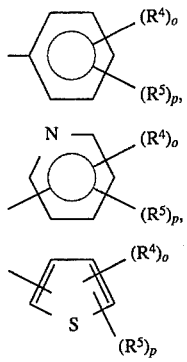

where $R^4$ and $R^5$ independently of one another are H, halogen, ($C_1$–$C_4$) alkyl, ($C_1$–$C_3$) alkoxy or a radical of the formula (D)

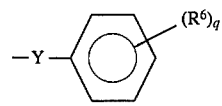

in which $R^6$ is H or halogen and
Y is $CH_2$, O or S, and
m, n, o, p and q are 0, 1 or 2, which comprises reacting a compound of the formula II

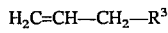

where $R^3$ is as defined in formula I, with dichloromethylsilane in the presence of a catalyst suitable for hydrosilylation reactions, and reacting the resulting intermediate of the formula III

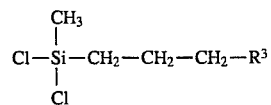

where $R^3$ is as defined in formula I, in succession and without isolation of the resulting intermediate, with a methylmagnesium halide and an arylmagnesium halide of the general formula IV

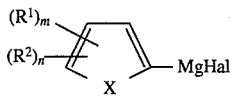

where $R^1$, $R^2$, m, n and X are as defined in formula I and Hal is halogen.

The intermediate formed, of the formula III, can be used for a further reaction by customary methods, either directly or after having been purified first.

The sequence of the reaction of the compound III with the Grignard reagents is exchangeable.

Suitable catalysts for hydrosilylation reactions are described by E. Lukevies and co-workers in J. Organometallic Chem. Library 5, pages 1–180 (1970). For example, they are complex salts of Pd(II), Pt(IV), Rh(I) or Ni(II), or Fe pentacarbonyl, and also organic peroxides in combination with UV irradiation. The use of hexachloroplatinic acid as the catalyst is preferred according to the invention.

The intermediates of the formula III are novel, and the invention relates to them as well as to their use for the preparation of active substances for plant protection agents.

The compounds of the formulae I, II and IV are known and are important as insecticidal, acaricidal or nematicidal active compounds or their precursors (see EP-A 0,224,024, EP-A 0,249,015, ZA 88/6875). These European Offenlegungsschriften describe processes for the preparation of these compounds, or their use in the preparation of the compounds I.

The synthesis of the compounds I starting from aryldimethylsilanes of the general formula V

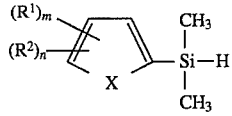

which are reacted with olefins of the formula II to give the active substances of the formula I, is known. However, in order to prepare the hydrosilanes V, chlorodimethylsilane is required, which is expensive and only available in small amounts. Alternatively, the hydrosilanes V may be prepared by the reduction of corresponding halo- or alkoxy-silanes, which is difficult on the industrial scale (EP-A 0,224,024).

Both shortcomings are overcome by the process according to the invention. In the synthesis sequence II-III-I which has been found, it was surprising that the formation of the compounds I from the intermediates III gave very high yields, since it could not have been predicted that the formation of monosubstitution products following a reaction of the compound III with one of the two Grignard reagents was selective. If high yields are to be achieved and if a complicated separation of the monosubstitution product of the formula VIa or VIb, which is initially desired, is to be avoided, it is imperative that the reaction of the intermediates III according to the invention is selective. Accordingly, the process according to the invention can be carried out as a one-pot reaction, a procedure which is not complicated to control.

When reacted with an equivalent of Grignard reagent, other dihalosilanes, such as, for example, dichlorodimethylsilane or methyldichlorosilane, give the monosubstitution product only in medium yields [1–6].

They are therefore often employed in large excess, which is uneconomical [1,2,6]. Another possibility to direct the reaction towards the monosubstitution product is first to exchange a halogen function for an amine radical, followed by a reaction with the organometal reagent and a subsequent conversion of the resulting aminosilane into the chlorosilane aimed at [7]). By virtue of the number of the reaction steps involved, this process is of course not highly suitable for large-scale industrial application.

When the reaction is directed appropriately, the intermediates III surprisingly react entirely selectively with an equivalent of Grignard reagent to give the intermediates of the general formula VIa or VIb, which are customarily not isolated;

1) K. A. Adrianov, N. V. Delazari, Doklady Akad. Nauk. SSSR 122, 393. Engl. Ed. S. 689;

2) R. N. Lewis, J. Amer. Chem. Soc. 70, 1115 (1948);

3) D. W. Lewis, G. C. Gainer, J. Amer. Chem. Soc. 74, 2931 (1952);

4) V. A. Ponomarenko, A. Snegova, Yu. P. Egorov, Izvest. Akad. Nauk. SSSR, Otdel Khim. Nauk 1960, 244; Engl. Ed. S. 222;

5) L. W. Breed, W. J. Haggerty jr., J. Org. Chem. 27, 257 (1962);

6) J. Hetflejs, F. Mares, V. Clevalovsky, Collection Czech. Chem. Commun. 30, 1643 (1965);

7) M. Takamizawa, M. Unemura (Shin-Etsu Chem. Industry Co., Ltd.), Jpn. Kokai Tokkyo Koko 79, 109, 923 (29.8.1979), Appl. 78/16063 (15.2.1978); C.A. 92, 146898v (1980);

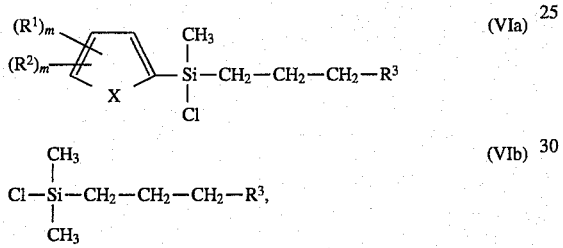

and which then together with the specific corresponding organometal component yield the compounds of the formula I. The best yields and the highest purities are achieved when the substitution of the first halogen atom is carried out at temperatures between −78° C. and +80° C., preferably at −20° C. to +30° C., the optimum temperature range varying depending on the organic radical of the Grignard reagent. The second halogen can then be replaced at any temperature desired within the interval −78° C. to +200° C., preferably 20° C.–100° C. Solvents which can be used are etheric solvents, such as, for example, diethyl ether, diisopropyl ether, dibutyl ether, tetrahydrofuran, glyme, diglyme, triglyme, tetraglyme or dioxane, as well as mixtures of the above with aliphatic or aromatic hydrocarbons, such as, for example, hexane, heptane, benzene, toluene or xylene. Tetrahydrofuran is preferred as the solvent. 1.00–1.05 moles, preferably 1.00–1.02 moles, of the Grignard reagent used for the first substitution are employed per mole of the intermediate of the general formula III. The organometal compound which serves for the second substitution is used in amounts of 1.00–1.10 moles, preferably 1.00–1.05 moles, per mole of the intermediate III. The amount of catalyst varies, and, for example in the case of Pt(IV) complex salts, is between 0.1–10 ppm relative to the reaction solution.

The reaction product (compound of the formula I) is worked up in a customary manner, for example by adding water, separating off the salt solution, and concentrating the organic phase. The crude product obtained can be purified further by distillation in vacuo.

The process according to the invention is illustrated by the examples which follows:

USE EXAMPLES

A) Preparation of a compound of the formula III

About 15 drops of a 30% strength hexachloroplatinic acid solution in isopropanol are mixed with 170.6 g (1.00 mol) of 4-fluoro-3-chloroallylbenzene, with stirring. About 15 ml of this mixture are subsequently metered into a reaction vessel under a nitrogen atmosphere, and about 10 ml of a total of 126.5 g (1.10 mol) of dichloromethylsilane are added. After heating at 50° C., the exothermal reaction starts. The remaining amounts of educt are now added from separate dropping funnels in such a way that the internal temperature remains between 85° and 95° C. Stirring is then continued at 90° C. for 2 hours. Distillation of the reaction mixture yields 233 g (81.6%) of dichloromethyl<3-(3-chloro-4-fluorophenyl)propyl>silane of boiling point$_{0.8}$ 103°–109° C.

B) Preparation of a compound of the formula I

A Grignard solution prepared from 97.8 g (0.487 mol) of 4-bromophenetol, 12 g of magnesium and 360 ml of THF is added dropwise at −20°±1° C. to a solution of 129.3 g (0.453 mol) of dichlorosilane, obtained in the previous example, in 250 ml of anhydrous THF. Stirring is then continued at −20° C. for 0.5 hours, and the mixture is then slowly allowed to reach room temperature. After 170 ml of 2.9 M methylmagnesium chloride solution in THF have been added, the mixture is refluxed for 1 hour and cooled to 30° C., and excess Grignard reagent is destroyed by the dropwise addition of 20 ml of water. The solvent is removed under a waterpump vacuum, and the residue is distributed between 700 ml of heptane and 500 ml of water. After the aqueous salt solution has been separated off, the organic phase is washed three times with 500 ml of water each time and then dried over $Na_2SO_4$ and concentrated. 162.7 g of a pale yellow oil are obtained. The distillation which follows yields 147.7 g (93%) of 4-ethoxyphenyldimethyl<3-(3-chloro-4-fluorophenyl)propyl>silane of boiling point $_{0.4}$ 158°–174° C. and in a purity of 97% (determination by gas chromatography).

The following compounds, inter alia, are obtained in high yields and high purity by following the principle of these instructions:

4-ethoxyphenyldimethyl<3-(3-phenoxyphenyl)propyl>silane 4-ethoxyphenyldimethyl<3-(4-fluoro-3-phenoxyphenyl)propyl>silane dimethyl-3,4-methylenedioxyphenyl<3-(3-phenoxyphenyl)propyl>silane 2-ethoxypyrid-5-yldimethyl<3-(3-phenoxyphenyl)propyl>silane dimethyl<2-(2,2,2-trifluoroethoxy)pyrid-5-yl>-<3-(4-fluoro-3-phenoxyphenyl)propyl>silane 2-ethylthiopyrid-5-yldimethyl<3-(4-fluoro-3-phenoxyphenyl)propyl>silane 2-ethoxythien-5-yldimethyl<3-(4-fluoro-3-phenoxyphenyl)propyl>silane 4-ethoxyphenyldimethyl<3-(6-phenoxypyrid-2-yl)propyl>silane <2-(2,2,2-trifluoroethoxy)pyrid-5-yl>dimethyl[3-<4-fluoro-3-(4-fluorophenoxy)phenyl>propyl]silane 4-ethoxyphenyldimethyl<3-(4-phenoxythien-2-yl)propyl>silane.

I claim:

1. A compound of the formula III

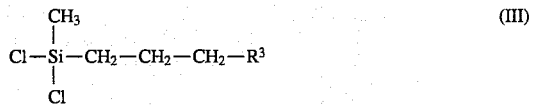

where R³ is a radical of the formulae (A), (B) or (C)

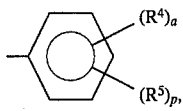 (A)

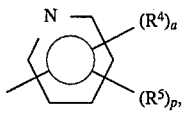 (B)

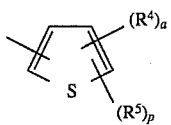 (C)

where R⁴ and R⁵ independently of one another are H, halogen, $(C_1-C_4)$alkyl, $(C_1-C_3)$alkoxy or a radical of the formula

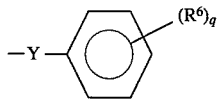 (D)

in which

R⁶ is H or halogen and

Y is $CH_2$, O or S, and o, p, q are the numbers 0, 1 or 2, provided that compound III is not dichloro-methyl-(3-phenylpropyl)-silane;

dichloro-[3-(4-chlorophenyl)-propyl]-methyl-silane;

dichloro-[3-(3-chlorophenyl)-propyl]-methyl-silane;

[3-(4-bromophenyl)-propyl]-dichloro-methyl-silane; or

[3-(3-bromophenyl)-propyl]-dichloro-methyl-silane.

* * * * *